United States Patent [19]
Mauskop

[11] Patent Number: 5,914,129
[45] Date of Patent: Jun. 22, 1999

[54] ANALGESIC COMPOSITION FOR TREATMENT OF MIGRAINE HEADACHES

[76] Inventor: Alexander Mauskop, 17A Lafayette Rd., Larchment, N.Y. 10538

[21] Appl. No.: 08/685,078

[22] Filed: Jul. 23, 1996

[51] Int. Cl.⁶ ....................................................... A61K 9/20
[52] U.S. Cl. ........................... 424/464; 424/465; 424/682
[58] Field of Search .............................. 424/44, 682, 692, 424/464.5; 514/165, 224.5, 350, 568, 728, 812

[56] References Cited

U.S. PATENT DOCUMENTS

| | | | |
|---|---|---|---|
| 2,801,951 | 8/1957 | Cooper | 167/65 |
| 3,359,166 | 12/1967 | McClure | 514/365 |
| 3,385,886 | 5/1968 | Nicholson et al. | 562/492 |
| 3,759,980 | 9/1973 | Rosen et al. | 560/143 |
| 3,865,933 | 2/1975 | Mudge | 424/195.1 |
| 4,083,951 | 4/1978 | Gouldie et al. | 424/44 |
| 4,217,340 | 8/1980 | Tobert | 424/157 |
| 5,538,959 | 7/1996 | Mauskop | 514/165 |

OTHER PUBLICATIONS

The Pharmacological Basis of Therapeutics, E.D.: Louis Goodman, The MacMillan Company, London, 1970, pp. 988, 989, 813, 316, 354, 359, 368, 315, 325, 326, Oct. 1970.
L.J. Ling et al., "Absorption of Iron After Experimental Overdose of Chewable Vitamins," *Am. J. Emerg. Med.* 9:24 (1991).
M. Coplin et al., "Tolerability of Iron: A Comparison of Bis–Glycino Iron II and Ferrous Sulfate," *Clin. Ther.* 13(5):606 (1991).
Goodman & Gilman's The Pharmaceutical Basis of Therapeutics 918, 1317–1325 (Joel G. Hardman et al. eds., 1996).
A.A. Krabbe et al., "Ferrumkvarts som profylaktikum ved migræ," *Useskr Læger ne* 142(8):516–18 (1980) (with English language translation).
J. Olesen et al., "Methodological Aspects of Prophylactic Drug Trials in Migraine," *Cephalalgia* 1:127–41 (1981).
B.M. Altura, "Calcium Antagonist Properties of Magnesium: Implications for Antimigrane Actions", Magnesium 4:169 (1985).
A. Mauskop et al., "Chronic Daily Headache—One Disease or Two? Diagnostic Role of Serum Ionized Magnesium", Cephalalgia 14:24 (1994).
A. Mauskop et al., "Deficiency in Serum Ionized Magnesium but not Total Magnesium in Patients with Migraines. Possible Role of $ICa^{2+}/IMg^{2+}$Ratio", Headache 33(3):135 (1993).
F. Facchinetti et al., "Magnesium Prophylaxis of Menstrual Migraine: Effects on Intacellular Magnesium", Headache 31(5):298 (1991).
K. Weaver, "Magnesium and Migraine", Letter to the Editor in Headache 30(2):168 (1990).
A. Foster et al., "Taking Apart NMDA Receptors", Nature 329: 395–396 (1987).

*Primary Examiner*—Jose' G. Dees
*Assistant Examiner*—Kathryne E. Shelborne
*Attorney, Agent, or Firm*—Pennie & Edmonds, LLP

[57] ABSTRACT

Magnesium-containing analgesic compositions used for the alleviation of pain, in particular, migraine headache pain, and methods for using the same are described herein. The compositions consist essentially of an analgesic agent, a magnesium salt, a stimulant, optionally an effervescing agent, and a pharmacetically acceptable carrier or vehicle. The symptoms of migraine headache intended to be alleviated include nausea, unilateral pain, dizziness, pulsatile pain, worsening of pain by light physical activity, photophobia and phonophobia.

28 Claims, No Drawings

ANALGESIC COMPOSITION FOR TREATMENT OF MIGRAINE HEADACHES

FIELD OF THE INVENTION

This invention relates to magnesium-based analgesic compositions for treating migraine headaches, and methods for using the same.

BACKGROUND OF THE INVENTION

Analgesic compositions comprising magnesium salts have been used to treat a variety of ailments as well as reduce the gastric irritancy often accompanying the oral administration of such analgesic compositions. U.S. Pat. 2,801,951 to Cooper, Jr. discloses the use of an analgesic composition comprising acetylsalicylic acid, citric acid, p-ethoxyacetanilide, caffeine and $MgCO_3$ or $Mg(OH)_2$/Al$(OH)_3$. U.S. Pat. No. 3,865,933 to Mudge teaches the use of a mixture comprising magnesium gluconate, stramonium extract and 3-(2-methylphenoxy)-1,2-propanediol to relieve headache pain. U.S. Pat. No. 3,759,980 to Rosen et al. teaches the use of a mixture of magnesium salicylate and choline salicylate as an analgesic, anti-pyretic, anti-inflammatory and anti-rheumatic agent. U.S. Pat. No. 3,385,886 to Nicholson et al. teaches the use of phenylpropionic acid magnesium salts for the relief of pain, fever and inflammation. U.S. Pat. No. 3,359,166 to McClure teaches the use of magnesium 4-thiazolidinecarboxylate as an analgesic agent. U.S. Pat. No. 4,083,951 to Goudie et al. teaches the use of magnesium acetylsalicylate in conjunction with sodium bicarbonate as an analgesic having reduced gastric irritancy properties. U.S. Pat. No. 4,217,340 to Tobert discloses the use of a phenylbenzoic acid compound and magnesium hydroxide for treating pain and inflammation. Such compositions have employed magnesium salts for their solubility, absorption properties and buffering effects.

A deficiency of magnesium, i.e., hypomagnesemia, has been suggested to play a role in migraine headaches (B.A. Altura, *Magnesium*, 4:169 (1985 ); A. Mauskop et al., *Cephalalgia*, 14:241 (1994 )). It had been shown that low serum ionized magnesium ($IMg^{2+}$) levels were found in 42 % of patients suffering migraine headaches (A. Mauskop et al., *Headache*, 33(3 ):135 (1993 )). The magnesium salt of pyrrolidone carboxylic acid has been used to treat women with premenstrual migraine headache (F. Facchinetti et al., *Headache*, 31(5 ):298 (1991 )). Amino-chelated magnesium compounds have been used to treat patients with classic migraine headache (K. Weaver in "Letter to the Editor," *Headache*, 30(2 ):168 (1990 )). In addition, $Mg^{2+}$ has been known to regulate the function of N-methyl-D-aspartate receptors (A. C. Foster et al., *Nature* (London), 329:395 (1987 )), which are essential for pain transmission.

When some magnesium-based compositions are administered to patients having migraines, severe headaches or other painful conditions, the slowing of gastric motility which often accompanies these conditions delays the absorption of any medication taken orally. Such a delay in absorption is often more pronounced with tablet than with liquid medicaments. As a result, the onset of action associated with such compositions administered to migraine patients is undesirably delayed, resulting in the prolongation of pain and discomfort to the patient. Thus, there remains a need for compositions which can be used for treating migraine headaches and which are rapidly absorbed and provide rapid onset of action.

In addition, because migraine headache is believed to be, at least in part, stress-induced, patients who suffer from migraine headaches often experience other secondary pain, e.g., muscle ache, joint stiffness, eye strain and jaw problems, associated with stress-related muscle tension. Where the patient is elderly or has still other painful health conditions, the combination with migraine and such secondary pain described above can be overwhelming. Thus there is a need for compositions which can be used for treating migraine headaches which contain analgesics or other compounds known to relive pain.

Moreover, oral administration of compositions comprising magnesium salts often results in the unwanted side effect of constipation, a feeling of bloatedness and short-term loss of appetite. Thus there is a need for compositions which can be used for treating migraine headaches which contain magnesium salts and do not give produce the above-described side effects following administration.

Citation or identification of any reference in this section shall not be construed as an admission that such reference is available as prior art to the present application.

SUMMARY OF THE INVENTION

The present invention relates to a method for treatment of migraine headaches which comprises orally administering to a person in need of such treatment a rapidly absorbed magnesium- and effervescing agent-containing analgesic composition in an amount effective to relieve at least some symptoms of such headaches. Such compositions include various proportions of an analgesic agent, a magnesium salt and an effervescing agent.

Prior to ingestion, such compositions are admixed with or dissolved in water, preferably in about 2–10 ounces of water. Such compositions are ingested as their aqueous admixture or solution, preferably within 1–2 minutes of admixture or dissolution.

The invention further relates to pharmaceutical compositions for alleviating pain, consisting essentially of a therapeutically effective amount of one or more magnesium salt, stimulant, and analgesic agent; and a pharmaceutically acceptable carrier or vehicle, wherein the composition is rapidly absorbed when orally administered.

The invention still further relates to pharmaceutical compositions for alleviating pain, consisting essentially of a therapeutically effective amount of one or more magnesium salt, stimulant, analgesic agent and effervescing agent; and a pharmaceutically acceptable carrier or vehicle, wherein the composition is rapidly absorbed when orally administered.

The present invention may be understood more fully by reference to the following detailed description and illustrative examples which are intended to exemplify non-limiting embodiments of the invention.

DETAILED DESCRIPTION OF THE INVENTION

According to the present invention, improved absorption and hence improved onset of action, as well as improved analgesia, of a preparation for treating a patient with a migraine headache can be achieved by administering to a patient with a migraine headache a magnesium-containing analgesic composition.

Such analgesic agents which can be included in the magnesium-containing analgesic compositions of the present invention include, but are not limited to, at least one or more non-opioid analgesic agent such as acetylsalicylic acid acetaminophen, paracetamol, ibuprofen, ketoprofen, ketoconazole, indomethacin, diflunisol, naproxen, ketorolac, dichlophenac, tolmetin, sulindac, phenacetin, piroxicam, mefamanic acid, dextromethorphan, other non-steroidal anti-inflammatory drugs including salicylates, pharmaceutically acceptable salts thereof and mixtures thereof; or at least one or more opioid analgesic agent such as codeine, morphine, hydromorphine, levophanol, meperidine, meptazinol, propoxyphene, propiram, buprenorphine, pentazocine, nalbuphine, butorphanol, tramadol, hydrocodone, oxycodone, methadone, pharmaceutically acceptable salts thereof and mixtures thereof. Such pharmaceutically acceptable salts include, but are not limited to hydrochloride, hydrobromide, phosphate, sulfate, acetate, succinate, ascorbate, tartrate, gluconate, benzoate, malate, fumarate, and the like. In addition, the present compositions can contain a combination of a non-opioid analgesic agent and an opioid analgesic agent, i.e., a mixture of at least one or more non-opioid analgesic agent, and at least one or more opioid analgesic agent.

The analgesic agent(s) of the magnesium-containing analgesic compositions of the present invention are useful for relieving pain, in particular pain associated with migraine symptoms, as well as pain associated with non-migraine illnesses aggravated by migraine pain. In the former instance, it is believed that the combination of a magnesium salt and the analgesic agent(s) exert(s) a synergistic effect for relieving pain and related migraine symptoms. In addition, the analgesic agent(s) can relieve pain associated with non-migraine illnesses. Common examples include muscle ache, joint stiffness, eye strain and jaw problems associated with stress-related muscle tension, as well as pain derived from non-stress related conditions. Where the pain is less than severe, non-opioid analgesics are preferred. Preferably, the non-opioid analgesics used in the present magnesium-containing analgesic compositions are acetaminophen or ibuprofen, or mixtures thereof.

Where the patient suffering from an illness, particularly a migraine headache, has particularly severe pain, or has additional pain from a non-migraine illness such that the combination of pain is judged to be severe, it may be necessary that the analgesic component of the magnesium-containing analgesic composition include an opioid analgesic capable of provided relief from severe pain. Such a regimen is also useful where the patient has a terminal illness such that liabilities resulting from long-term administration of an opioid are outweighed by the interest in the patient's short-term comfort.

In a particular embodiment of the invention, the magnesium-containing analgesic compositions include more than one analgesic agent, i.e., at least two different non-opioid analgesic agents, at least two different opioid analgesic agents, or at least one non-opioid analgesic agent and at least one opioid analgesic agent. It is believed that combinations of non-opioid analgesic agents, or opioid analgesic agents, or both, act synergistically to relieve pain.

The magnesium component of the magnesium-containing analgesic compositions of the present invention is ionic magnesium (i.e., $Mg^{2+}$). Suitable sources of $Mg^{2+}$ are magnesium salts which include, but are not limited to magnesium chloride, magnesium citrate, magnesium tartrate, magnesium oxide, magnesium carbonate, magnesium sulfate, magnesium hydroxide and mixtures thereof. It is to be understood that the present compositions can include one or more magnesium salt. Where an analgesic agent to be included in the magnesium-containing compositions is a carboxylic acid, the magnesium salt can be a magnesium salt of that analgesic agent carboxylic acid. For example, if the analgesic agent is acetylsalicylic acid, the magnesium salt can be magnesium acetylsalicylate. This is convenient in combining both important components within a single compound. When a magnesium salt of an analgesic is included in the magnesium-containing analgesic composition of the present invention, an additional analgesic may or may not be included.

It is advantageous for the compositions to be rapidly absorbed by the subject or patient following oral administration. By "rapidly absorbed" is meant that the present compositions are absorbed through the gastrointestinal tract within about 5 to about 20 minutes following ingestion.

There are a number of ways to formulate such compositions to achieve rapid absorption, and one of ordinary skill in the art would be aware of such ways. Generally, encapsulating the active ingredient or employing other forms of delaying the release of the agent into the subject should be avoided, except when such means to delay release are included in combination with a rapidly absorbed form of such agent. This could be used, for example, when the composition is intended to provide both a rapidly absorbed initial administration of the analgesic agent, followed by a delayed release of longer duration administered for continued relief of headache symptoms.

In one embodiment of a rapidly absorbable magnesium-containing analgesic composition, one or more effervescing agent is included. By "effervescing agent" is meant any compound which, upon dissolution in water, provides effervescence to the aqueous mixture or solution upon release of carbon dioxide. Such effervescing agents include, but are not limited to, alkali or alkaline earth metal carbonates, bicarbonates or mixtures thereof, including, but not limited to sodium carbonate, sodium bicarbonate, sodium glycine carbonate, calcium carbonate and magnesium carbonate. Preferably, at least one of the effervescing agents is sodium bicarbonate.

In another embodiment of the invention, the magnesium-containing compositions include one or more stimulant, such as methamphetamine, deoxamphetamine, methylphenidate, pemoline and preferably, caffeine, and mixtures thereof. Inclusion of a stimulant, inter alia, allows the present compositions to be rapidly absorbed. Without being bound to any particular theory, it is believed that such stimulants, particularly caffeine, stimulate gastric secretion and accordingly enhance absorption through the small intestine. In the case of caffeine, it is believed that magnesium cation forms a relatively stable chelate therewith, such that the caffeine serves to rapidly deliver the magnesium to the small intestine and increase its rate of absorption. Thus, the stimulant component serves to confer rapid absorption properties to the present compositions. In addition, it is believed that caffeine itself has analgesic properties (see Federal Register, 42(131):35482–35485 (1977)) which can serve to diminish the discomfort of pain, particularly pain associated with migraine headaches.

In addition to serving as a means to enhance the absorption of the present magnesium-containing analgesic compositions, the inclusion of a stimulant also serves to diminish the discomfort of constipation or a feeling of bloatedness, or relieve the temporary loss of appetite often following ingestion of opioids, which are known to be binding and are known to produce the aforementioned side effects, and counteract the gastric stasis associated with migraine headaches. In this regard, a stimulant diminishes or relieves the discomfort of these side effects by moderately stimulating peristalsis. It is within the purview of one skilled in the art to tailor the present compositions so as to provide the optimal dosage of stimulant.

Moreover, the inclusion of a stimulant serves to counteract the sedative, or in extreme cases where an analgesic is an opioid analgesic, hallucinatory effects of the analgesic. In other words, the incorporation of a stimulant improves the patient's motor coordination, alertness and overall sense of well being.

It is to be understood that the present magnesium-containing analgesic compositions can include both an effervescing agent and a stimulant, so as to further enhance the absorbability of the present compositions.

The magnesium-containing analgesic compositions further include a pharmaceutically acceptable carrier or vehicle. Such carriers or vehicles are known to those skilled in the art and are found, for example, in *Remingtons's Pharmaceutical Sciences,* 14th Ed. (1970 ). Examples of such carriers or vehicles include lactose, starch, dicalcium phosphate, calcium sulfate, kaolin, mannitol and powdered sugar. Additionally, when required, suitable binders, lubricants, disintegrating agents and coloring agents can be included. If desired, dyes, as well as sweetening or flavoring agents can be included.

The magnesium-containing analgesic compositions may optionally include accessory ingredients including, but not limited to dispersing agents such as microcrystalline cellulose, starch, cross-linked poly(vinyl pyrrolidone), and sodium carboxymethyl cellulose; flavoring agents; coloring agents; binders; preservatives; surfactant and the like.

The non-opioid analgesic agent(s) is (are) advantageously present in the magnesium-containing compositions at levels ranging from about 10 to about 90 wt. %, preferably about 10 to about 75 wt. %.

The opioid analgesic agent(s) is (are) present in the magnesium-containing compositions at levels ranging from about 0.5 to about 20 wt. %, preferably from about 1 to about 15 wt. %.

It is to be understood that the present compositions can contain an analgesic agent such that the analgesic agent is a mixture of one or more non-opioid analgesic agent and one or more non-analgesic agent. In such a case, the non-opiate analgesic agent(s) is (are) present in the magnesium-containing compositions at levels ranging from about 10 to about 90 wt. %, preferably about 10 to about 75 wt. %; and the opioid analgesic agent(s) is (are) present in the magnesium-containing compositions at levels ranging from about 0.5 to about 20 wt. %, preferably from about 1 to about 15 wt. %.

When added as a separate component, i.e., not as a magnesium salt of an analgesic agent, the magnesium salt(s) is (are) present in the magnesium-containing compositions at levels ranging from about 5 to about 30 wt. %, preferably from about 10 to about 30 wt. %. When a single compound of a magnesium salt of the analgesic agent is used, the amounts of such a single compound would be between about 20 and 95 wt. % of the composition.

When present, the effervescing agent(s) is (are) present in the magnesium-containing compositions at levels ranging from about 20 to about 80 wt. %, preferably from about 25 to about 75 wt. %.

The stimulant(s) is (are) present in the magnesium-containing analgesic compositions at levels ranging from about 1 to about 25%, preferably from about 5 to about 20 wt. %.

Of course, the total amounts of these components would be 100 wt. %, and those of ordinary skill in the art can vary the amounts within the stated ranges to achieve useful compositions.

The intended route of administration of the magnesium-containing analgesic compositions of the present invention is oral, wherein the composition including an effervescing agent is admixed with or dissolved in a pre-determined amount of an aqueous vehicle, such as for example water, prior to ingestion. The present compositions not including effervescing agents are not admixed with or dissolved in water prior to administration.

Compositions of the present invention which are suitable for oral administration may be presented as discrete units such as capsules, cachets or tablets, as a powder or granules; as a solution or a suspension in an aqueous liquid or non-aqueous liquid; or an oil-in-water or water-in-oil liquid emulsion. Preferably, the compositions of the present invention is presented in liquid, capsule, or most preferably, tablet form. Such tablets may be conventionally formed by compression or molding. Compressed tablets may be prepared by compressing in a suitable machine the mixture of one or more analgesic, magnesium salt, stimulant, optionally an effervescing agent, and a pharmaceutically acceptable carrier or vehicle described above. Molded tablets may be made by molding in a suitable machine the above mixture which can optionally be moistened with an inert liquid diluent. The tablets may optionally be coated or scored, having indicia inscribed thereupon, and may be so formulated as to provide slow or controlled release of the analgesic, magnesium or effervescing compounds therein.

Such tablets can range in weight from 25–2000 mg., preferably from 100–1000 mg., and most preferably from 250–1500 mg.

Prior to ingestion, compositions comprising effervescing agents are admixed or dissolved in about 2–10 ounces of an aqueous carrier such as water, preferably about 4–8 ounces of water. The compositions of the present invention are ingested as their aqueous admixture or solution within 2 minutes, preferably within 1 minute, of their admixture with or dissolution in water, so as to maximize their effervescence and hence absorptive properties.

Compositions not comprising effervescent agents are ingested, in the case of liquid compositions, neat (undiluted), and in the case of capsules or tablets, swallowed whole, preferably with water.

The compositions of the present invention are administered shortly after the onset of migraine symptoms. Such symptoms include nausea, unilateral pain, dizziness, pulsatile pain, worsening of pain by light activity, photophobia and phonophobia.

Administration can continue every 2–6 hours, preferably every 4 hours until migraine symptoms have subsided. In patients who suffer from chronic migraine headaches, a daily administration of 1000 mg. of the magnesium-containing compositions four times per day of the present invention is advantageous.

The following series of examples are presented by way of illustration and not by way of limitation on the scope of the invention.

EXAMPLES OF MAGNESIUM-CONTAINING ANALGESIC COMPOSITIONS

EXAMPLE 1

Magnesium-Containing Analgesic Composition A

| Ingredient | mg./Tablet |
| --- | --- |
| Acetylsalicylic Acid | 800 |
| Magnesium Chloride | 250 |
| Sodium Bicarbonate | 500 |
| Poly(ethylene Glycol) 4000 | 50 |

EXAMPLE 2

Magnesium-Containing Analgesic Composition B

| Ingredient | mg./Tablet |
| --- | --- |
| Magnesium Acetylsalicylic Acid | 1000 |
| Sodium Bicarbonate | 350 |
| Citric Acid | 75 |

EXAMPLE 3

Magnesium-Containing Analgesic Composition C

| Ingredient | mg./Tablet |
| --- | --- |
| Acetaminophen Na Salt | 1000 |
| Magnesium Tartrate | 200 |
| Magnesium Carbonate | 200 |

EXAMPLE 4

Magnesium-Containing Analgesic Composition D

| Ingredient | mg./Tablet |
| --- | --- |
| Ibuprofen | 400 |
| Magnesium Chloride | 225 |
| Caffeine | 80 |
| Carboxymethyl cellulose | 50 |

EXAMPLE 5

Magnesium-Containing Analgesic Composition E

| Ingredient | mg./Tablet |
| --- | --- |
| Magnesium Acetylsalicylic Acid | 1000 |
| Methamphetamine | 75 |
| Starch | 75 |

EXAMPLE 6

Magnesium-Containing Analgesic Composition F

| Ingredient | mg./Tablet |
| --- | --- |
| Acetaminophen Na Salt | 1000 |
| Magnesium Tartrate | 200 |
| Magnesium Carbonate | 200 |
| Caffeine | 100 |
| Codeine Sulfate | 45 |

EXAMPLE 7

Magnesium-Containing Analgesic Composition G

| Ingredient | mg./Tablet |
| --- | --- |
| Ibuprofen | 500 |
| Magnesium Chloride | 225 |
| Caffeine | 80 |
| Carboxymethyl cellulose | 50 |
| Sodium Bicarbonate | 500 |

EXAMPLE 8

Magnesium-Containing Analgesic Cocktail

The tablet of Examples 1–3, 6 or 7 is added to 8 ounces of tap water. The resulting cocktail is ingested within 1 minute of admixture with or dissolution in water.

EXAMPLE 9

Results of Administration of Magnesium-Containing Analgesic Cocktail to Patients with Migraine Headaches Methods Five subjects were selected to participate in this study. Included were patients who had daily, but not necessarily continuous migraine headaches. Patients could have had headache-free periods lasting for hours and on a rare occasion for a day. Average severity of headaches prior to and two hours following administration of the magnesium-containing analgesic cocktail described below were assessed on a 1 to 10 verbal scale. Patients taking acetaminophen or non-steroidal anti-inflammatory drugs were excluded from this study.

Magnesium-Containing Analgesic Cocktail

Three tablets each having the following formulation:

| Ingredient | mg./Tablet |
| --- | --- |
| Acetylsalicylic acid | 325 |
| Sodium Bicarbonate | 1916 | were dissolved in a solution of 500 mg of magnesium sulfate in 7 ounces of water and administered to each of five patients suffering migraine headache by ingestion of the resulting cocktail within 1 minute of dissolution of each of the three tablets. The results, compiled from a survey of each patient taken 2 hours following ingestion of the cocktail are show below in Table 1:

TABLE 1

RESULTS

| N | Age | Sex | Severity Prior to Administration | Severity Following Administration |
|---|-----|-----|----------------------------------|-----------------------------------|
| 1 | 33  | F   | 10                               | 4                                 |
| 2 | 35  | F   | 7                                | 2                                 |
| 3 | 14  | F   | 8                                | 3                                 |
| 4 | 59  | F   | 7                                | 1                                 |
| 5 | 30  | M   | 8                                | 2                                 |

Thus for all patients included in this study, the administration of the above-described magnesium-containing analgesic composition significantly reduced the severity of migraine headaches.

EXAMPLE 10

Reduction of Migraine Symptoms Following Intravenous Administration of MgSO$_4$

Methods

Forty consecutive patients (3 men and 37 women) who presented with an acute migraine but did not have renal, cardiac or other medical problems were administered with 1 g. of MgSO$_4$ in a 10% saline solution intravenously, over 5 minutes. Patients remained in a recumbent position during the infusion and for 5 minutes after the infusion. Headache intensity was measured on a verbal 1 to 10 scale before, and 15 minutes after, the infusion. The recurrence or worsening of a headache within the following 24$h$ was determined using the verbal 1 to 10 scale in a telephone interview. A greater than 50% reduction of pain intensity lasting at least 24h was considered a positive response.

Results

Of the 40 patients, 35 (87.5%) had a reduction of pain of 50% or more 15 minutes after the infusion. This included 9 patients who experienced complete relief. In 21 of these 35 patients, at least this degree of improvement or complete relief persisted for 24h or more (positive response).

Thus, the administration of magnesium salt is effective at relieving the symptoms of migraine headache.

The magnesium-containing analgesic compositions of the present invention can be used to treat patients with migraine headaches. It is to be understood that such uses are not limited to treating the symptoms of migraine headaches but rather include treating other maladies including non-migraine headache pain, muscular pain, fever associated with viral or bacterial infection, thrombotic diathesis, magnesium deficiency and gastric discomfort.

The present invention is not be limited in scope by the specific embodiments disclosed in these examples which are intended to illustrate the most preferred embodiments of the invention. Indeed, various modifications of the invention or other embodiments which are functionally equivalent to those shown and described herein will become apparent to those skilled in the art and are intended to be covered by the appended claims.

A number of references have been cited, the entire disclosures of which are incorporated herein by reference.

What is claimed:

1. A pharmaceutical composition for the alleviation of pain, associated with migraine headache consisting essentially of a therapeutically effective amount of one or more magnesium salt, one or more stimulant selected from the group consisting of methamphetamine, deoxamphetamine, methylphenidate, pemoline, caffeine and mixtures thereof, and one or more analgesic agent selected from the group consisting of acetylsalicylic acid, acetaminophen, paracetamol, ibuprofen, ketoprofen, ketoconazole, indomethacin, diflunisol, naproxen, ketorolac, dichlophenac, tolmetin, sulindac, phenacetin, piroxicam. mefamanic acid, dextromethorphan, codeine, morphine, hydromorphine, levophanol, meperidine, meptazinol, propoxyphene, yropiram, buprenorphine, pentazocine, nalbuphine, butorphanol, tramadol, hydrocodone, oxycodone and methadone, pharmaceutically acceptable salts thereof, and mixtures thereof; and a pharmaceutically acceptable carrier or vehicle, wherein the composition is orally administered.

2. The composition of claim 1, wherein at least one of the one or more analgesic agent is a non-opioid analgesic agent.

3. The composition of claim 2, wherein the non-opioid analgesic agent is selected from the group consisting of acetylsalicylic acid, acetaminophen, paracetamol, ibuprofen, ketoprofen, ketoconazole, indomethacin, diflunisol, naproxen, ketorolac, dichlophenac, tolmetin, sulindac, phenacetin, piroxicam, mefamanic acid, dextromethorphan, salicylates, pharmaceutically acceptable salts thereof, and mixtures thereof.

4. A pharmaceutical composition for the alleviation of pain, associated with migraine headache consisting essentially of a therapeutically effective amount of one or more magnesium salt, one or more stimulant, and one or more analgesic agent selected from the group consisting of acetylsalicylic acid, acetaminophen, paracetamol, ibuprofen, ketoprofen, ketoconazole, indomethacin, diflunisol, naproxen, ketorolac, dichlophenac, tolmetin, sulindac, phenacetin, piroxicam, mefamanic acid, dextromethor-han, codeine, morphine, hydromorohine, levophanol, meperidine, meptazinol, propoxyphene, propiram, buprenorphine, pentazocine, nalbuphine, butorphanol, tramadol, hydrocodone, oxycodone and methadone, pharmaceutically acceptable salts thereof, and mixtures thereof, wherein at least one of the one or more analgesic agent is an opioid analgesic agent; and a pharmaceutically acceptable carrier or vehicle, wherein the composition is orally administered.

5. The composition of claim 4, wherein the opioid analgesic agent is selected from the group consisting of codeine, morphine, hydromorphine, levophanol, meperidine, meptazinol, propoxyphene, propiram, buprenorphine, pentazocine, nalbuphine, butorphanol, tramadol, hydrocodone, oxycodone and methadone, pharmaceutically acceptable salts thereof, and mixtures thereof.

6. A pharmaceutical composition for the alleviation of pain, associated with migraine headache consisting essentially of a therapeutically effective amount of one or more magnesium salt, one or more stimulant, and one or more analgesic agent selected from the group consisting of acetylsalicylic acid, acetaminophen, paracetamol, ibuprofen, ketoprofen, ketoconazole, indomethacin, diflunisol, na-roxen, ketorolac, dichlophenac, tolmetin, sulindac, phenacetin, piroxicam, mefamanic acid, dextromethorphan, codeine, morphine, hydromorphine, levophanol, meperidine, meptazinol, propoxyphene, propiram, buprenorphine, pentazocine, nalbuphine, butorphanol, tramadol, hydrocodone, oxycodone and methadone, pharmaceutically acceptable salts thereof, and mixtures thereof, wherein the one or more analgesic agent is a combination of a non-opioid analgesic agent and an opioid analgesic agent;

and a pharmaceutically acceptable carrier or vehicle, wherein the composition is orally administered.

7. The composition of claim 1, wherein at least one of the one or more magnesium salt is a magnesium salt of an analgesic agent.

8. The composition of claim 7, wherein the magnesium salt of the analgesic agent is magnesium acetylsalicylate.

9. The composition of claim 1, wherein the one or more magnesium salt is present at a level ranging from about 5 to about 30 wt. %, and the one or more stimulant is present at a level ranging from about 1 to about 25%.

10. The composition of claim 1, wherein at least one of the one or more analgesic agent is a non-opioid analgesic agent and is present at a level ranging from about 10 to about 90 wt. %.

11. The composition of claim 4, wherein the opioid analgesic agent is present at a level ranging from about 0.5 to about 20 wt. %.

12. The composition of claim 6, wherein the non-opioid analgesic agent is present at a level ranging from about 10 to about 90 wt. %, and the opioid analgesic agent that is present at a level ranging from about 0.5 to about 20 wt. %.

13. A pharmaceutical composition for the alleviation of pain, associated with migraine headache consisting essentially of a therapeutically effective amount of one or more magnesium salt, one or more stimulant selected from the group consisting of methamphetamine, deoxamphetamine, methylphenidate, pemoline, caffeine and mixtures thereof, one or more analgesic agent selected from the group consisting of acetylsalicylic acid, acetaminophen, paracetamol, ibuprofen, ketoprofen, ketoconazole, indomethacin, diflunisol, naproxen, ketorolac, dichlophenac, tolmetin, sulindac, phenacetin, piroxicam, mefamanic acid, dextromethorphan, codeine, morphine, hydromorphine, levophanol, meperidine, meptazinol, propoxyphene, propiram, buprenorphine, pentazocine, nalbuphine, butorphanol, tramadol, hydrocodone, oxycodone and methadone, pharmaceutically acceptable salts thereof, and mixtures thereof and one or more effervescing agent; and a pharmaceutically acceptable carrier or vehicle, wherein the composition is orally administered.

14. The composition of claim 13, wherein at least one of the one or more analgesic agent is a non-opioid analgesic agent.

15. The composition of claim 14, wherein the non-opioid analgesic agent is selected from the group consisting of acetylsalicylic acid, acetaminophen, paracetamol, ibuprofen, ketoprofen, ketoconazole, indomethacin, diflunisol, naproxen, ketorolac, dichlophenac, tolmetin, sulindac, phenacetin, piroxicam, mefamanic acid, dextromethorphan, salicylates, pharmaceutically acceptable salts thereof, and mixtures thereof.

16. A pharmaceutical composition for the alleviation of pain, associated with migraine headache consisting essentially of a therapeutically effective amount of one or more magnesium salt; one or more stimulant; one or more analgesic agent selected from the group consisting of acetylsalicylic acid, acetaminophen, paracetamol, ibuprofen, ketoprofen, ketoconazole, indomethacin, diflunisol, naproxen, ketorolac, dichlophenac, tolmetin, sulindac, phenacetin, piroxicam, mefamanic acid, dextromethorphan, codeine, morphine, hydromorphine, levophanol, meperidine, meptazinol, propoxypmhene, propiram, buprenorphine, pentazocine, nalbuphine, butorphanol, tramadol, hydrocodone, oxycodone and methadone, pharmaceutically acceptable salts thereof, and mixtures thereof, wherein at least one of the one or more analgesic agent is an opioid analgesic agent; one or more effervescing agent; and a pharmaceutically acceptable carrier or vehicle, wherein the composition is orally administered.

17. The composition of claim 16, wherein the opioid analgesic agent is selected from the group consisting of codeine, morphine, hydromorphine, levophanol, meperidine, meptazinol, propoxyphene, propiram, buprenorphine, pentazocine, nalbuphine, butorphanol, tramadol, hydrocodone, oxycodone and methadone, pharmaceutically acceptable salts thereof, and mixtures thereof.

18. A pharmaceutical composition for the alleviation of pain, associated with migraine headache consisting essentially of a therapeutically effective amount of one or more magnesium salt; one or more stimulant; one or more analgesic agent selected from the group consisting of acetylsalicylic acid, acetaminophen, paracetamol, ibuprofen, ketoprofen, ketoconazole, indomethacin, diflunisol, naproxen, ketorolac, dichlophenac, tolmetin, sulindac, phenacetin, piroxicam, mefamanic acid, dextromethorphan, codeine, morphine, hydromorphine, levophanol, meperidine, meptazinol, propoxyphene, propiram, buprenorphine, pentazocine, nalbuphine, butorphanol, tramadol, hydrocodone, oxycodone and methadone, pharmaceutically acceptable salts thereof, and mixtures thereof, wherein at least one of the one or more analgesic agent is a non-opioid analgesic agent, and at least one of the one or more analgesic agent is an opioid analgesic agent; one or more effervescing agent; and a pharmaceutically acceptable carrier or vehicle, wherein the composition is orally administered.

19. The composition of claim 13, wherein at least one of the one or more magnesium salt is a magnesium salt of an analgesic agent.

20. The composition of claim 19, wherein the magnesium salt of the analgesic agent is magnesium acetylsalicylate.

21. The composition of claim 13, wherein the one or more effervescing agent is selected from the group consisting of alkali or alkaline earth metal carbonates, bicarbonates and mixtures thereof.

22. The composition of claim 13, wherein at least one of the one or more magnesium salt is present at a level ranging from about 5 to about 30 wt. %, and the one or more stimulant is present at a level ranging from about 1 to about 25 wt. %.

23. The composition of claim 13, wherein at least one of the one or more analgesic agent is a non-opioid analgesic agent and is present at a level ranging from about 10 to about 90 wt. %.

24. The composition of claim 16, wherein the opioid analgesic agent is present at a level ranging from about 0.5 to about 20 wt. %.

25. The composition of claim 18, wherein the non-opioid analgesic agent is present at a level ranging from about 10 to about 90 wt. %, and the opioid analgesic agent is present at a level ranging from about 0.5 to about 20 wt. %.

26. The composition of claim 13, wherein the one or more effervescing agent is present at a level ranging from about 20 to about 80 wt. %.

27. A pharmaceutical composition for the alleviation of pain, associated with migraine headache consisting essentially of from about 5 to about 30 wt. % of one or more magnesium salt, from about 1 to about 25 wt. % of one or more stimulant selected from the group consisting of methamphetamine, deoxamphetamine, methylphenidate, pemoline, caffeine and mixtures thereof, and analgesic agent selected from the group consisting of an opioid analgesic agent, an non-opioid analgesic agent and mixtures thereof, the non-opioid analgesic agent being selected from the group consisting of acetylsalicylic acid, acetaminophen, paracetamol, ibuprofen, ketoprofen, ketoconazole, indomethacin, diflunisol, naproxen, ketorolac, dichlophenac, tolmetin, sulindac, phenacetin, piroxicam, mefamanic acid and dextromethorphan, and pharmaceutically acceptable salts thereof; and the opioid analgesic agent being selected from the group consisting of codeine, morphine, hydromorphine, levophanol, meperidine, meptazinol, propoxyphene, propiram, buprenorphine, pentazocine, nalbuphine, butorphanol, tramadol, hydrocodone, oxycodone and methadone, and pharmaceutically acceptable salts thereof, wherein the opioid analgesic agent is present in an amount of from about 0.5 to about 20 wt. %, and the non-opioid analgesic agent is present in an amount from about 10 to about 90 wt. %; and a pharmaceutically acceptable carrier or vehicle, wherein the composition is orally administered.

28. A pharmaceutical composition for the alleviation of pain, associated with migraine headache consisting essentially of from about 5 to about 30 wt. % of one or more magnesium salt, from about 1 to about 25 wt. % of one or more stimulant selected from the group consisting of methamphetamine, deoxamphetamine, methylphenidate, pemoline, caffeine and mixtures thereof, from about 20 to about 80 wt. % of one or more effervescing agent, and analgesic agent selected from the group consisting of an opioid analgesic agent, an non-opioid analgesic agent and mixtures thereof, the non-opioid analgesic agent being selected from the group consisting of acetylsalicylic acid, acetaminophen, paracetamol, ibuprofen, ketoprofen, ketoconazole, indomethacin, diflunisol, naproxen, ketorolac, dichlophenac, tolmetin, sulindac, phenacetin, piroxicam, mefamanic acid and dextromethorphan, and pharmaceutically acceptable salts thereof; the opioid analgesic agent being selected from the group consisting of codeine, morphine, hydromorohine, levophanol, meperidine, mentazinol, propoxhene, propiram, buprenorohine, pentazocine, nalbuphine, butorphanol, tramadol, hydrocodone, oxycodone and methadone, and pharmaceutically acceptable salts thereof, wherein the opioid analgesic agent is present in an amount of from about 0.5 to about 20 wt. %, and the non-opioid analgesic agent is present in an amount from about 10 to about 90 wt. % and a pharmaceutically acceptable carrier or vehicle, wherein the composition is orally administered.

* * * * *

UNITED STATES PATENT AND TRADEMARK OFFICE
CERTIFICATE OF CORRECTION

PATENT NO. : 5,914,129

DATED : June 22, 1999

INVENTOR(S) : Alexander Mauskop

It is certified that error appears in the above-indentified patent and that said Letters Patent is hereby corrected as shown below:

On the title page, item [76], delete "Larchment" and insert --Larchmont--.

Signed and Sealed this

Twenty-sixth Day of October, 1999

Attest:

Q. TODD DICKINSON

*Attesting Officer*   *Acting Commissioner of Patents and Trademarks*